United States Patent [19]
House

[11] Patent Number: 6,090,075
[45] Date of Patent: *Jul. 18, 2000

[54] DISPOSABLE URINARY CATHETERIZATION ASSEMBLY

[76] Inventor: Jamie Glen House, 7200 Almeda, Apt. 201, Houston, Tex. 77054

[*] Notice: This patent issued on a continued prosecution application filed under 37 CFR 1.53(d), and is subject to the twenty year patent term provisions of 35 U.S.C. 154(a)(2).

[21] Appl. No.: 09/052,309

[22] Filed: Mar. 31, 1998

[51] Int. Cl.[7] .......................... A61M 5/00; A61M 25/00; A61M 27/00
[52] U.S. Cl. .......................... 604/172; 604/523; 604/544
[58] Field of Search .................................. 604/167, 170, 604/171, 172, 256, 265, 523, 533, 544; 206/571; 600/581, 574

[56] References Cited

U.S. PATENT DOCUMENTS

| | | | |
|---|---|---|---|
| 3,683,928 | 8/1972 | Kuntz | 128/349 R |
| 3,757,771 | 9/1973 | Ruegg et al. | 128/2.1 E |
| 3,825,001 | 7/1974 | Bennett et al. | 128/214.4 |
| 3,854,483 | 12/1974 | Powers | 128/349 R |
| 3,894,540 | 7/1975 | Bonner, Jr. | 128/349 R |
| 3,991,762 | 11/1976 | Radford | 128/276 |
| 4,170,996 | 10/1979 | Wu | 128/349 R |
| 4,205,690 | 6/1980 | Layton | 128/768 |
| 4,230,115 | 10/1980 | Walz, Jr. et al. | 128/295 |
| 4,246,909 | 1/1981 | Wu et al. | 128/762 |
| 4,569,344 | 2/1986 | Palmer | 128/207.16 |
| 4,638,539 | 1/1987 | Palmer | 29/157 R |
| 4,652,259 | 3/1987 | O'Neil et al. | 604/54 |
| 4,692,154 | 9/1987 | Singery et al. | 604/172 |
| 4,776,848 | 11/1988 | Solazzo | 604/247 |
| 4,811,847 | 3/1989 | Reif et al. | 206/571 |
| 4,834,711 | 5/1989 | Greenfield et al. | 604/172 |
| 5,045,078 | 9/1991 | Asta | 604/329 |
| 5,073,164 | 12/1991 | Hollister et al. | 604/43 |
| 5,084,036 | 1/1992 | Rosenbaum | 604/329 |
| 5,096,454 | 3/1992 | Samples | 604/54 |
| 5,147,341 | 9/1992 | Starke et al. | 604/349 |
| 5,209,726 | 5/1993 | Goosen | 604/54 |
| 5,226,530 | 7/1993 | Golden et al. | 206/210 |
| 5,460,616 | 10/1995 | Weinstein et al. | 604/167 |
| 5,573,520 | 11/1996 | Schwartz et al. | 604/282 |
| 5,582,599 | 12/1996 | Daneshvar | 604/263 |
| 5,613,956 | 3/1997 | Patterson et al. | 604/256 |

*Primary Examiner*—Mark O. Polutta
*Assistant Examiner*—Michael J. Hayes
*Attorney, Agent, or Firm*—Conley, Rose & Tayon

[57] ABSTRACT

A disposable self-lubricating catheterization assembly for inserting a catheter into the urethra of an individual for the purpose of evacuating the bladder is disclosed. The catheter assembly includes a substantially rigid catheter introducer member for positioning the introducer against the urethral opening, a flexible catheter and a flexible thin-walled sheath surrounding the catheter and partially covering the catheter introducer. The catheter introducer comprises a reservoir portion, a guide portion, lubricant and a membrane. The lubricant essentially fills the reservoir and is prevented by the membrane from prematurely coating the catheter, in order to facilitate grasping of the catheter and feeding of the tube along the urethra and into the bladder. A catheterization assembly in accordance with the present invention is suitable for use for self-catheterization in the home or in a public restroom, and deters contamination and subsequent infection of the urinary tract. The improved easy-to-use disposable catheterization kit is also economically practical for use for temporary catheterizations in hospitals, mobile emergency facilities, doctors' offices, rehabilitation facilities, nursing homes and the like.

22 Claims, 5 Drawing Sheets

DISPOSABLE URINARY CATHETERIZATION ASSEMBLY

BACKGROUND OF THE INVENTION

The present invention relates generally to catheter devices and more particularly to urinary catheters having protective sheaths, lubricating means, and means for facilitating insertion of the catheter into the urethra.

It has become relatively commonplace for the occasional, intermittent or periodic catheterization of an individual's urinary bladder to be employed, as opposed to placement and maintenance of an indwelling catheter that continuously drains urine from the bladder. Short term, or repeated catheterization is appropriate, or even required, for many persons who are in a hospital setting, a nursing home, doctor's office, rehabilitation facility or in the home. For example, a patient is sometimes catheterized to treat such conditions as urinary retention, the inability to evacuate urine, or for the purpose of obtaining a sterile urine specimen from a patient in a doctor's office.

The need for intermittent catheterization of an individual sometimes arises due to problems typically associated with long term use of indwelling catheters, such as infections, urethral damage, bladder damage. Long term use of an indwelling catheter is also a risk factor for bladder cancer. This is often the case for persons having a neurogenic urinary condition, such as in a spinal cord injury, multiple sclerosis, stroke, trauma or other brain injury. Conditions that interfere with the individual's ability to voluntarily void the bladder may also arise post-surgically or as a result of benign prostatic hypertrophy or diabetes. Many of the affected individuals are capable of, and would prefer to perform self-catheterization. For many, the level of risk and discomfort of repeated catheterizations carried out over the course of a day (at 3–6 hour intervals, for example) are offset by the accompanying convenience, privacy or self-reliance that is achieved. Some of the major difficulties that arise in self-catheterization are the lack of satisfactory cathaterization kits, the problem of maintaining the required level of sanitation during the procedure, and the difficulty of sometimes performing the procedure under conditions of restricted space and privacy.

In assisted, or non self-catheterizations, it is common practice in hospitals to employ a catheterization tray, which typically includes a sterile drape, gloves, a conventional catheter, antiseptic solution, swabs, lubricant, forceps, underpad and a urine collection container. Assisted catheterization is usually performed with the patient in a supine position. Maintaining a sterile field during the procedure can still be a problem, however, and the "cath tray" procedure is impractical for use with some individuals and situations today.

Since it is inconvenient and thus undesirable to have to use a conventional cath tray and maintain strictly sterile technique, there have been many efforts in the past to simplify the catheterization procedure, and to "unitize" the equipment to facilitate sanitary practice and to make urine collection easier and quicker. For example, U.S. Pat. No. 4,230,115, issued to Walz, Jr. et al., describes a catheter and collection receptacle combination in which the catheter is initially enclosed in a sterile bag. U.S. Pat. No. 4,246,909, issued to Wu et al., describes another catheter within a collection bag, the bag also having means for isolating a clean urine specimen. U.S. Pat. No. 4,652,259, issued to O'Neil, is for a catheter assembly designed to prevent carrying periurethral microorganisms into the upper urethra and bladder along with the catheter. U.S. Pat. No. 5,147,341, issued to Starke et al., is drawn to another catheter and collection bag combination that provides for transiting the periurethral region prior to introduction of the catheter.

The catheters of many of the prior art devices are lubricated just before use by means of a tube of conventional lubricant, such as K-Y Jelly™, after removal from their sterile packaging. This practice is not only inconvenient, but is a potential source of microbial contamination. U.S. Pat. No. 5,209,726, issued to Goosen, describes one type of self-lubricating catheter enclosed in a type of close-fitting flexible sheath. Upon insertion into the urethra, the lubricant-filled sheath collapses upon the catheter and forces lubricant out the tip of the catheter and along the urethra, as the catheter progresses inwardly toward the bladder. U.S. Pat. No. 5,226,530, issued to Golden, is for a catheter with its pre-lubricated tip partially enclosed in a smaller secondary package. The smaller package serves to localize the lubricant on the tip area and to prevent the lubricant from spreading throughout the interior of the larger package and over the entire catheter. U.S. Pat. No. 5,582,599, issued to Daneshvar, has a type of clear protective cover assembly intended, in part, to prevent contamination of the catheter during handling. The catheter is grasped through a type of flexible cover, that may have interior projections to facilitate grasping a prelubricated or medicated catheter. U.S. Pat. No. 3,894,540, issued to Bonner, Jr., is for a catheter designed for intermittent use, having a collapsable flexible cover that deters bending or kinking of the catheter.

Many individuals with spinal cord injuries or other neurological diseases routinely perform intermittent catheterization several times a day using conventional catheters or kits and "clean technique." Clean technique means that the urethral area is initially swabbed with antiseptic, and efforts are made to avoid contamination of the catheter during the procedure. The user's hands are not sterile and a sterile field is not maintained. Clean technique is used instead of sterile technique, generally, for two reasons. First, it is very difficult, if not impossible, for individuals who are performing self-catheterization to adhere strictly to sterile technique. Secondly, these individuals are required to catheterize themselves between 3 and 6 times a day, and the cost of a new sterile catheter and the accessories required to perform sterile catheterization becomes excessively expensive for some users. Sometimes an individual will reuse a "cleaned" catheter. As a result, the use of "clean technique" will many times result in contamination and subsequent infection of the urinary tract, causing significant morbidity and cost to the patient and society.

Even if cost considerations were not a major consideration for the user, with most of the prior art self-contained sterile units where the collection bag doubles as the catheter insertion cover, the catheter is extremely difficult for the user to grasp and insert. This is particularly a problem for self-catheterization users who may also have neurologic problems that limit manual dexterity. Also, with some of the available catheter kits and methods, the catheter is either not sufficiently lubricated during insertion (and thus requires the additional application of possibly non-sterile lubricant), or the catheter is too slick with lubricant and cannot effectively be grasped through the insufficiently flexible bag. As a practical matter, most individuals who would prefer to self-catheterize cannot do so using the existing apparatus while maintaining the required level of sanitation.

Another difficulty with the prior art's propensity for merely sterilely packaging the catheter inside the urine collection bag is that the flexible bag is typically neither thin-walled and pliant enough to permit grasping and feeding the catheter into the urethra, nor is it sufficiently rigid for accurate urine output measurement or for specimen removal. With some of the available catheter kits, there is also the further problem of the proximal end of the catheter tending to drop down into the collection bag. In this circumstance, the user must first maneuver the catheter tip back to the bag opening before the catheter can be inserted into the patient's urethral opening.

Accordingly, there is a need for an easy-to-use disposable catheter system that is economically practical for use for temporary catheterizations by individuals or by health care providers in hospitals, mobile emergency facilities, doctors' offices, rehabilitation facilities, nursing homes and the like. Also, there is a need for a disposable catheter assembly that provides substantial ease of use for self-catheterization, in the home or in a public restroom, and that provides a high degree of sanitation during handling and use. Moreover, if an easier to use catheterization kit were available that could be economically manufactured and purchased for one time only use, the incidence of urethral and bladder infections in catheterization patients would undoubtedly improve.

SUMMARY OF THE INVENTION

The present invention provides a new catheter assembly that permits essentially sterile catheterization of the bladder and establishment of free drainage of urine from the distal end of the catheter without using conventional sterile field technique. The new catheter assembly is an improvement over existing "unitized" self-lubricating catheters, many of which combine a catheter with a waste collection bag and is an economic and desirable alternative to conventional catheterization trays used by health care personnel. The new catheter assembly is simple to use for either assisted or self-catheterization, with the individual in either a supine or non-supine position. The invention and its method of use provide a decreased risk of contamination and infection over prior "unitized" assemblies, and provide for easy waste disposal or collection for measurement or analysis using a conventional container.

In accordance with the present invention, a catheterization assembly is provided that generally includes a catheter introducer member with a throughbore that is open on both ends. In certain embodiments, a portion of the throughbore between the two openings forms a lubricant chamber for containing a catheter lubricant. A piercable membrane is located in the throughbore and is able to retain the lubricant in the lubricant chamber. In some embodiments, the throughbore is of essentially uniform diameter from end to end, and in other embodiments the portion of the throughbore that forms the lubricant chamber is of increased diameter. The catheter introducer member may have a reservoir portion, which contains the lubricant chamber and the first end of the throughbore. It may also have a guide portion that contains the second throughbore end. In some embodiments the reservoir portion and the guide portion are releasably connected to each other. In some embodiments, the catheterization assembly also includes a catheter tube that has its tip extending through the second opening of the throughbore. The tip of the catheter is able to pierce the membrane when it is forced against the membrane. The guide portion may include a tapered surface that is serves to guide the catheter tip into the second opening of the throughbore.

Certain preferred embodiments of the catheterization assembly also have a sheath that envelops a length of the catheter, the sheath being attached to the catheter at a location that is spaced apart from the first end of the throughbore. The sheath is also attached to the guide member in such a way that the second opening of the throughbore is also enveloped by the sheath. The length of the sheath is approximately the same as the length of covered catheter so that when the sheath is fully stretched lengthwise, the first end, or tip, of the catheter is held in an initial position that is inside of the guide, between the second end of the throughbore and the pierceable membrane. In some embodiments there is a removable closure on the first opening of the throughbore. In certain embodiments of the new catheterization assembly, the lubricant chamber is tapered or substantially frustoconical in shape, and the membrane is positioned at the widest end of the tapered chamber. The tapered surface also serves to direct the catheter tip toward the throughbore outlet into the urethra. The membrane is located between the lubricant chamber and the guide portion of the catheter introducer and is able to be pierced by catheter to form an aperture in the membrane. Preferably the membrane is a thin, flat disk made of silicon, or a similar resilient material, and it may be pre-scored or slit to facilitate piercing by the catheter. In some embodiments the membrane includes an annular ring or ridge, and the catheter guide member may accordingly include an annular lip that sealingly engages a raised annular ring on the membrane.

Preferably the outer surfaces of the catheterization assembly are smooth, but some embodiments may include a roughened or textured outer surface on the catheter introducer, to facilitate grasping of the catheter introducer.

In certain embodiments of the catheterization assembly of the present invention the catheter introducer member has monolithic guide and reservoir portions, and the membrane is fixed between the guide and reservoir portions. In certain other embodiments, the guide portion and the reservoir portion are separate members that are joined together in such a way that they can be detached from each other. The guide member may have an annular ridge and the reservoir member may have an annular recess, the annular ridge and annular recess capable of being mated and joined together in such as way that they can be separated.

Also provided in accordance with the present invention is a kit for catheterizing a urinary bladder. The kit includes a sterilizable catheterization assembly such as described above. The assembly is housed in a sterility-maintaining package, and the kit also includes one or more antiseptic swabs.

A preferred embodiment of the present invention is a disposable self-lubricating catheter assembly for inserting a catheter into the urethra of an individual for the purpose of evacuating the bladder. The catheter assembly generally includes a catheter introducer for positioning the introducer against the urethral opening, a flexible catheter, and a flexible thin-walled sheath. The catheter introducer may also have a grip-enhanced outer surface, if desired. The flexible catheter is of a suitable length and has appropriate internal and external diameters. The catheter introducer has a longitudinal throughbore with a bore diameter that is at least as large as the catheter outer diameter, so that the catheter can rotate and slide through the narrowest portions of the throughbore. The catheter introducer is made up of two primary sections, a reservoir portion and a catheter guide portion, which are either formed together as a single piece or as separable pieces having compatible throughbores. The proximal end of the reservoir is designed to be placed against the external urethral opening with the throughbore outlet aligned with the urethra. In some embodiments, the throughbore of the reservoir portion enlarges to form an interior space, or cavity, that holds a lubricant gel. The shape of the lubricant cavity, or chamber, is such that the lubricant is not merely extruded into the urethra by the catheter, but is made such that the lubricant adheres to the surface of the catheter as it passes through the chamber.

There is a membrane or diaphragm situated between the interior space and the guide portion. The membrane holds the lubricant inside the reservoir until it is needed for lubricating the tip and the outside surface of the catheter. The membrane, which may include a resilient annular ring, also helps to seal the reservoir/guide connection such that the joint is resistant to infiltration by outside contaminates. In certain embodiments, the guide has a recessed lip that is situated for sealingly engaging a raised annular ring on the membrane. The sheath is made of a thin-walled, flexible material, preferably transparent, with its length and diameter chosen such that the sheath substantially covers the catheter and the distal end of the catheter guide. The tube-like sheath is closed around the guide distal end of the guide and around the catheter near its distal end to form a space, or lumen. The length and manner of attachment of the sheath is chosen such that, in the unused condition, the tip and a predetermined length or segment of the catheter is held inside the throughbore of the guide but below the membrane. In the insertion configuration, the membrane has been pierced by the tip of the catheter such that the tube protrudes through an aperture in the membrane, into the reservoir, and the tube outer surface includes a lubricant coating.

The present invention also provides a catheter introducer module for attachment to a conventional urinary catheter and then sterilized after assembly. The module includes a catheter guide with a central longitudinal throughbore having an internal diameter approximating the external diameter of a urinary catheter. The length and diameter of the catheter to be used with the introducer module is selected according to the size and particular needs of the individual. The catheter introducer module also has a reservoir portion with a tapered portion that widens to define an interior cavity retaining the lubricant. A membrane is situated between the reservoir interior cavity and the reservoir distal end, or the proximal end of the guide. The proximal end of the reservoir portion is designed for contacting the individual's external urethral opening in such a way that the urethra and the throughbores of the module are aligned. In some embodiments of the module, the guide proximal end and the reservoir distal end are releasably joined together, by friction fit or snap fit of overlapping bores, such that the throughbores are in communication and the connection is substantially resistant to microbial or other contaminant penetration. Some embodiments of the module also include a thin-walled pliable sheath, of compatible length and diameter, that substantially covers the distal end of the catheter guide and is able to substantially cover a preselected urinary catheter to provide a catheter assembly similar to the embodiments described above, which can be sterilized as a unit.

BRIEF DESCRIPTION OF THE DRAWINGS

For a detailed description of a preferred embodiment of the invention, reference will now be made to the accompanying drawings wherein.

DETAILED DESCRIPTION OF THE PREFERRED EMBODIMENTS

Figure 1A:
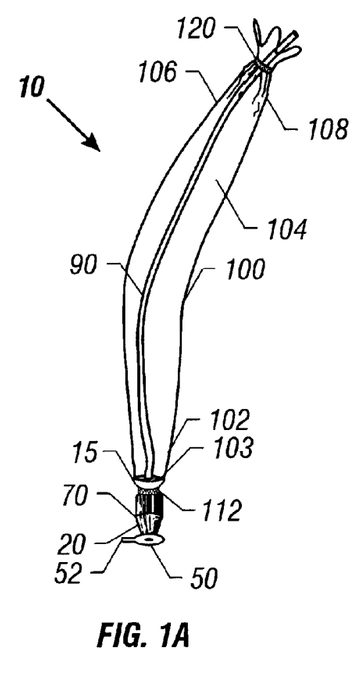
FIG. 1A is an elevation view of an embodiment of the urinary catheterization assembly of the present invention.
Figure 2A:
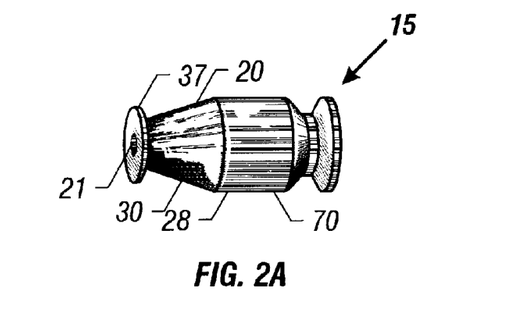
FIG. 2A is an elevational view of a self-lubricating catheter introducer of the catheterization assembly of FIG. 1A.

Referring first to FIG. 1A, a catheter assembly 10 according to the present invention generally includes a catheter introducer 15, a catheter 90, a thin-walled pliable sheath 100, and first and second sheath closures 112, 120. Catheter 90 is preferably similar to, or the same as, a conventional urinary catheter. The catheter introducer 15, shown in FIGS. 2A–B, includes a reservoir member 20 and a catheter guide member 70, with a membrane or diaphragm 40 disposed therebetween. Catheter guide 70 and reservoir 20 are preferably made of rigid or semi-rigid transparent or translucent plastic or silicon, but another similar material may be used as long as it is biocompatible, sterilizable and sufficiently inflexible to support the catheter during insertion.

Figure 2B:
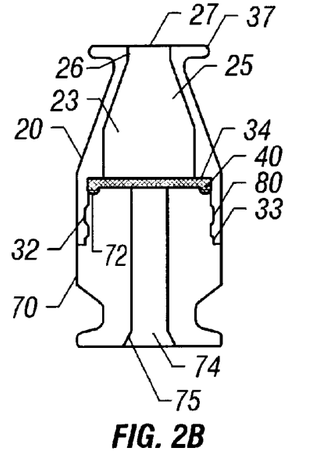
FIG. 2B is a side elevational view, in cross section, of the catheter introducer of FIG. 2A.
Figure 2C:
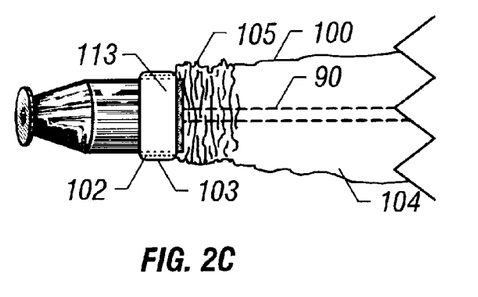
FIG. 2C is an elevational view of another embodiment of a catheterization assembly of the present invention.
Figure 2D:
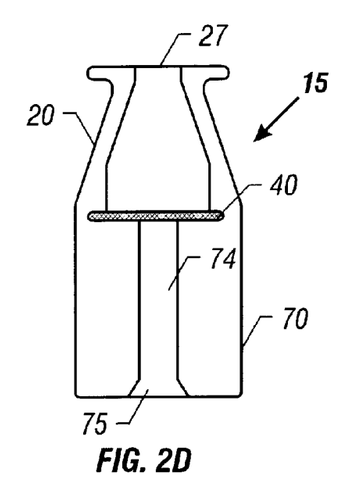
FIG. 2D is a side elevational view, in cross-section, of an alternative embodiment of the catheter introducer portion of the assembly shown in FIG. 2C.
Figure 3A:
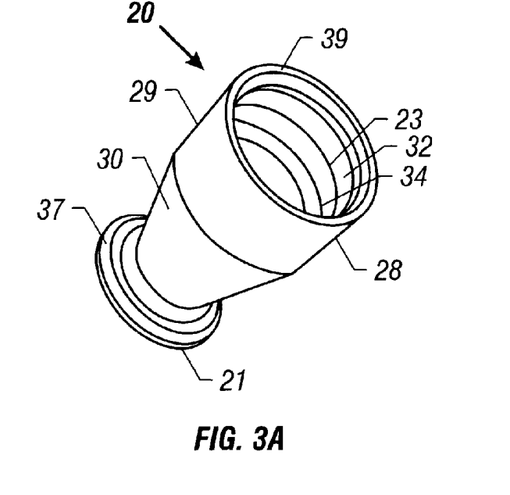
FIG. 3A is a perspective view showing the distal end of the reservoir portion of the lubricating catheter introducer of FIGS. 2A–B.
Figure 3B:
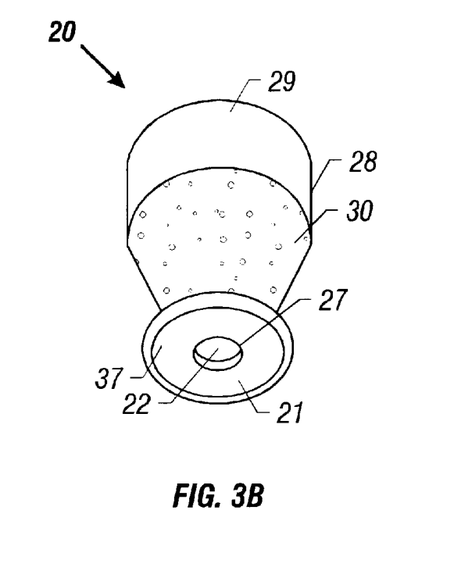
FIG. 3B shows the proximal end of the reservoir of FIG. 3A.
Figure 3C:
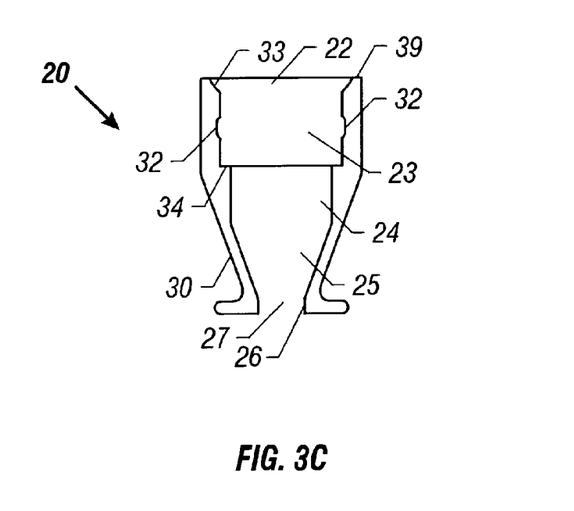
FIG. 3C is a side view, in cross-section, of the reservoir portion of the catheter introducer as shown in FIGS. 2A–B.
Figure 4A:
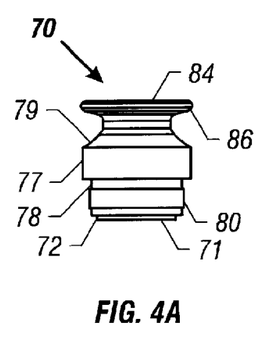
FIG. 4A is a side elevational view of the catheter guide portion of the self-lubricating catheter introducer shown in FIGS. 2A–B.
Figure 4B:
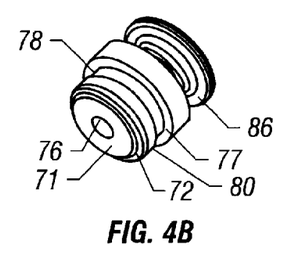
FIG. 4B is a perspective view of the catheter guide of FIG. 4A showing the proximal end of the guide.
Figure 4C:
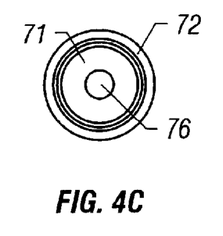
FIG. 4C is an end view of the catheter guide of FIG. 4A shown from the proximal end.
Figure 4D:
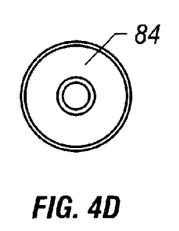
FIG. 4D is an end view of the catheter guide of FIG. 4A shown from the distal end.
Figure 4E:
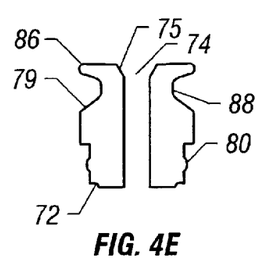
FIG. 4E is a cross sectional view of the guide shown in FIG. 4A.
Figure 4F:
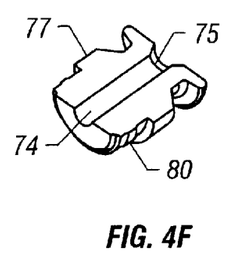
FIG. 4F is a perspective cross sectional view of the guide shown in FIG. 4B.

Referring now to FIGS. 3A–C, reservoir member 20 generally includes proximal end 21, distal end 39, an outer surface 28 extending between ends 21, 39 and a central throughbore 22. Disposed at proximal end 21 is a body contacting collar or flange 37. Outer surface 28 includes a generally cylindrical segment 29 adjacent distal end 39, and a frustoconical segment 30 that extends between cylindrical segment 29 and flange 37. Throughbore 22 includes a plurality of coaxially aligned bore segments, including receptacle portion 23 that is adjacent distal end 39, a reduced diameter portion 24, a tapered portion 25 and a neck portion 26 that is adjacent to proximal end 21. An annular ledge or lip 34 is formed in throughbore 22 between receptacle portion 23 and reduced diameter portion 24. Receptacle portion 23 includes a beveled edge 33 at distal end 39 and an annular recess or groove 32 formed between lip 34 and beveled edge 33. If desired, cylindrical portion 29 and/or frustoconical segment 30 may include a roughened or textured surface (as shown in FIG. 3B), which may be created during casting of reservoir member 20 or by scoring or machining of outer surface 28. Alternatively, throughbore 23 may have an essentially uniform diameter from end 21 to end 39 (similar in appearance to throughbore 74 shown in FIGS. 2B and 2D), for ease of manufacturing.

Figure 5A:
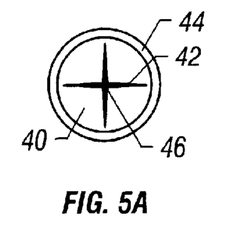
FIG. 5A is a top view of the retention membrane shown in FIGS. 2B.
Figure 5B:
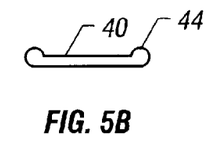
FIG. 5B is a side profile view of the membrane shown in FIG. 5A.

Catheter guide member 70, best shown in FIGS. 4A–F, is a generally cylindrical member having a coupling portion 78, a sheath retaining portion 79 and a central portion 77 disposed therebetween. Guide member 70 further includes a proximal end 71, a distal end 84, and a central throughbore 74. Throughbore 74 includes an outlet 76 adjacent proximal end 71, and a tapered inlet 75 adjacent distal end 84, best shown in FIGS. 4E–F. Sheath retaining portion 79 includes a sheath retaining collar 86 at distal end 84 and an annular recess or neck 88 between collar 86 and central portion 77. Coupling portion 78 is substantially cylindrical and may include an annular lip 72 at proximal end 71 and an annular ridge or protrusion 80 disposed between lip 72 and central portion 77. As shown in FIG. 2B and described in more detail below, coupling portion 78 is sized so as to be matingly received within receptacle portion 23 of reservoir member 20. Referring to FIG. 2B, disposed between annular lip 72 of guide member 70 and annular ledge 34 of reservoir member 20 is a trapping membrane or diaphragm 40. As shown in FIGS. 5A–B and 2B, membrane 40 may include a raised annular ring 44 that engages annular lip 72 of guide 70 and annular ledge 34 of reservoir 20 to form a good seal. Preferably, membrane 40 is made of silicon or similar elastomeric material capable of sealing and retaining lubricant 60 and capable of withstanding a conventional sterilization procedure. Membrane 40 includes a central scored portion 42 to facilitate piercing by the tip or proximal end 92 of catheter 90 to form a central aperture 46. Alternatively, the central scored portion 42 may be precut or slit, and due to the resiliency of the membrane material, the slit region remains closed sufficient to retain the lubricant in the lubricant chamber, until the catheter tip is pushed against the central region 42 of the membrane to force an opening or aperture in the slit.

Figure 5C:
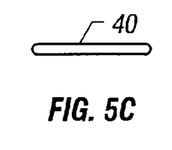
FIG. 5C is a side profile view of an alternative embodiment of the membrane shown in FIG. 5B.

As shown in FIG. 5C, the raised annular ring 44 may be omitted from resilient membrane 40, if desired, and annular lip 72 of guide 70 may be omitted, for ease of manufacturing. In this case, membrane 40 is held tightly between proximal end 71 of guide 70 and annular lip 72 of reservoir 20.

Figure 1B:
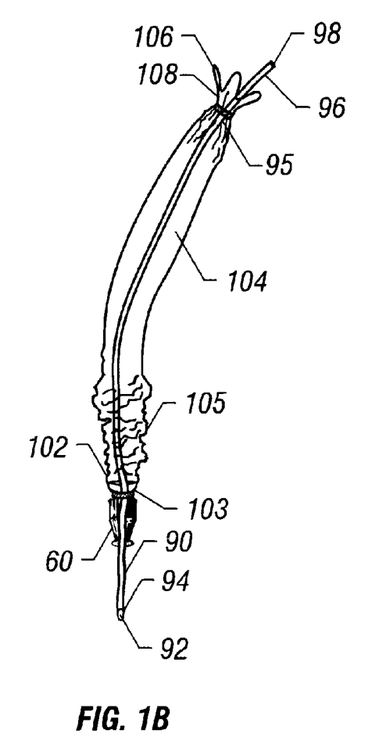
FIG. 1B shows the catheterization assembly shown in FIG. 1A with the catheter partially extended, as during insertion.

Referring to FIGS. 1A–B and 2B, catheterization assembly 10 further includes a flexible catheter 90 having proximal and distal ends 92 and 96, respectively. Near proximal end 92 is urine inlet 94, and at the terminus of distal end 96 is urine outlet 98. Initially, proximal end 92 of catheter 90 is slidably and rotatably received within throughbore 74 of guide 70 and disposed at a location between membrane 40 and tapered inlet 75. Catheter 90 is held in place by throughbore 74 and by a thin-walled pliable sheath 100. Sheath 100 has a proximal end 102, a distal end 106, a lumen 104 and closure points 103, 108. Closure point 103 near proximal end 102 is fixedly attached to guide 70 in annular recess 88, and closure point 108 near distal end 106 is fixedly attached to catheter 90 at closure point 108 adjacent distal end 106 that coincides with sealing point 95, adjacent outlet 98, of catheter 90, such that sheath 100 encloses catheter 90 from annular recess 88 of guide 70 to a point 95 along catheter 90 near the distal end 96. The interior or lumen 104 of sheath 100 is large enough to permit catheter 90 to rotate and slide therein when the sheathing material collapses and is gathered up during use, yet is not so large that the sheath is cumbersome. For example, using a conventional red latex catheter of about 5 mm external diameter, the sheath diameter is preferably about 1.5 to 2.5 inches (3.81–6.35 cm).

As shown in FIGS. 1A–B, sheath 100 is attached at closure points 103 and 108 by first and second sheath closures 112, 120, which may be plastic or elastomeric ties or bands. The length of catheter that is covered by the sheath between sheath closure points 103 and 108, is at least the length that will be inserted into the urethra, plus the length that stays in the catheter introducer module, plus the length that is needed to remain outside of the catheter guide portion for accommodating the gathered up sheathing.

In preferred embodiments of the invention, a sterile lubricant 60 substantially fills reduced diameter portion 24 and tapered portion 25 of reservoir 20. Lubricant 60 is initially retained therein by a removable closure such as sealing tape 50 (FIG. 1A), which may be adhesively attached to body contacting collar 37 of proximal end 21 to cover aperture 26, and by membrane 40. Optionally, a removable close-fitting cap over proximal end 21 of catheter introducer module 15 may be substituted for tape 50 and tab 52.

Referring now to FIG. 2B, catheter introducer 15 is assembled by disposing membrane 40 of catheter assembly 10 against lip 34 in throughbore 22 of reservoir member 20. The coupling portion 78 of guide 70 is then inserted into receptacle portion 23 of reservoir 20 until annular ridge 80 is captured within annual recess 32 of reservoir 20. Proximal end 92 of catheter 90 is then inserted into tapered inlet 75 and throughbore 74 of guide 70, and is then further inserted until proximal end 92 is adjacent to membrane 40. Care is taken so as not to prematurely pierce membrane 40 during this assembly step. Proximal end 102 of sheath 100 is next disposed about annular recess 88 of guide 70 and fastened thereto by closure band 112. Similarly, band 120 attaches distal end 106 of sheath 100 to catheter 90 at closure point 108.

Reduced diameter portion 24 and tapered portion 25 of reservoir 20 are then filled with lubricant 60, which retains its lubricating properties during sterilization. Lubricant 60 is preferably a soft gel such as K-Y Lubricating Jelly™, but another biocompatible liquid or gel may be substituted as long as it provides adequate lubrication and does not appreciably leak through aperture 46 of membrane 40. Once filled, tape strip 50 is placed over aperture 27 of proximal end 21 to retain lubricant 60 within the interior cavity of reservoir 20. In an alternative embodiment (not shown), reservoir 20 is omitted and a suitable lubricant 60 is contained in a narrow throughbore 23 resembling throughbore 74 shown in FIGS. 2B and 2D. This embodiment may be preferred for ease of manufacturing.

Thus assembled, catheterization assembly 10, including lubricant 60 and tape 50, is sterilized in accordance with standard practices for similar medical devices, such as conventional irradiation techniques. The catheter assembly is then stored in a sterile disposable wrapper until needed. In certain embodiments, the catheter assembly is part of a kit that includes one or more antiseptic-soaked swabs. Optionally, the kit may also contain gloves, a specimen container and/or a urine measuring container.

Catheterization assembly 10 is employed as follows. After first cleansing the urethral area, the person performing the catheterization removes tape 50 from body contacting collar 37 by pulling on a non-adherant portion, tab 52, to uncover aperture 27 of reservoir member 20 Outlet 98 of catheter distal end 96 is positioned, optionally, for collection into a measuring device, a portable waste receptacle, a toilet, or a specimen container. One particular feature of the catheterization assembly of the present invention is that it may be conveniently attached to a collection device with precise measuring marks, to permit more accurate measurement of urine output than is typically possible with conventional disposable catheterization assemblies.

It is important to note that the user's hands, while preferably being clean, do not have to be strictly "sterile" for this procedure, as long as care is taken not to directly touch the area of the urethral opening or the catheter during the catheterization. It is also important that the user not disconnect guide member 70 and reservoir member 20, or otherwise breach the seal provided by membrane annular ring 44 such that outside contaminants can be introduced into the sterile interior of catheter introducer 15.

Grasping catheter introducer 15 about outer surface 28, the body contacting collar 37 is then disposed against the urethral opening such that aperture 27 of reservoir member 20 is aligned axially with the urethral opening. The catheter 90 is grasped through the soft, flexible sheathing material 100 near the sheath retaining collar 86 of catheter guide 70 and the proximal end 92 is manually advanced in throughbore 74 until the scored central portion 42 of membrane 40 has been punctured or pierced by proximal end 92 of catheter 90. This method forms a tight fitting central aperture 46 in membrane 40 through which proximal end 92 of catheter 90 protrudes. As previously described, membrane 40 is preferably a thin, flat membrane of elastomeric material, but it may be shaped differently, as long as it functions in the same way to initially keep the sterile lubricant 60 from contacting catheter 90, and is puncturable or penetrable to form a snug fitting aperture 46 about catheter 90.

Upon moving proximal end 92 through guide 70 and into reservoir 20, the resulting excess length of sheath 100 is drawn up and becomes gathered 105 adjacent the sheath retaining collar 86, as illustrated in FIG. 1B. By appropriately repositioning the user's grasp on catheter 90 through sheath 100 and continuing to gently urge catheter 90 along throughbores 22, 74, the proximal end 92 proceeds through reduced diameter portion 24 and tapered portion 25 of reservoir 20 where the exterior surface 93 encounters and becomes coated with lubricant 60. While continuing to hold catheter introducer module 15 in place against the urethral opening, the user's grasp on catheter 90 through sheath 100 is repeatedly repositioned, as necessary, for optimally continuing to urge the lubricant coated catheter 90 along throughbores 22, 74, through tapered portion 25 and neck 26, out aperture 27, into the urethral opening, along the urethra and finally into the bladder a sufficient distance to permit draining of accumulated urine. Tapered portion 25 and neck 26 also serve to guide catheter 90 into alignment with aperture 27. The internal diameters of throughbores 22, 74, reservoir aperture 27, membrane aperture 46, guide tapered inlet 75 and guide outlet 76 are made slightly larger than the outer diameter of catheter 90, so that the catheter, even when well coated with lubricant 60, can move slightly radially and can slide longitudinally. The throughbore diameters 22, 74 are restrictive enough, however, that the catheter introducer module 15 prevents the flexible catheter 90 from bending and provides the catheter 90 with sufficient rigidity and support to be readily inserted into the urethra.

As necessary, catheter introducer 15 is held in place at the urethral opening and catheter 90 is supported through sheath 100 until completion of urine evacuation and removal of catheter 90. Catheter 90 is withdrawn from the urethra essentially by reversing the insertion procedure to resume the pre-use position. After withdrawal, catheter 90 is again disposed within sheath 100 and guide 70 and is ready for easy disposal of the unit in a sanitary manner. The entire catheterization process can usually be accomplished in about 5 minutes.

Using the new catheter assembly provides for better lubrication of the catheter to reduce the discomfort or irritation typically associated with urethral catheterization. This assembly is also an improvement over known unitized catheter assemblies in that it provides more options for the user, i.e., disposal of waste in a conventional toilet, collection of a specimen for analysis, or accurate measurement of urine output using conventional containers without having to first open a collection bag. It is more adaptable for use in the home or in a public restroom, and lends itself more readily for use in self-catheterization. The procedure described above enables the user to easily maintain sterile technique to avoid introduction of microbial contaminants into the upper urethra and bladder. Also, the new catheterization assembly provides a degree of protection to medical personnel from directly contacting a catheter that may have been exposed to body fluids possibly contaminated with virus. The catheter assembly exemplified herein can be manufactured economically for use by hospitals, emergency care facilities, nursing homes, rehabilitation centers and the like.

Referring to FIG. 2D, an alternative embodiment of catheter introducer 15 is shown. Instead of catheter introducer 15 being made up of reservoir member 20 and guide member 70, as separable pieces, the catheter introducer unit may be an integral, or monolithic structure with membrane 40 imbedded between the reservoir portion 20 and the catheter guide portion 70 (as shown in FIG. 2D). The embodiment of FIG. 2D may be preferred for ease of manufacture and for cost considerations.

In another embodiment of catheter assembly 10 (shown in FIG. 2C), annular recess 88 of catheter guide 70 is omitted, as are ties 112, 120, and sheath end 112 is instead held firmly in place by a compression ring 113. Other means of attaching the sheath to the catheter introducer could also be substituted, such as heat fusion, an adhesive or glue, as long as contaminants are sufficiently excluded by the closures during handling of the catheterization assembly. The embodiment of FIG. 2C may be preferred for ease of manufacture and for cost considerations.

Figure 6:
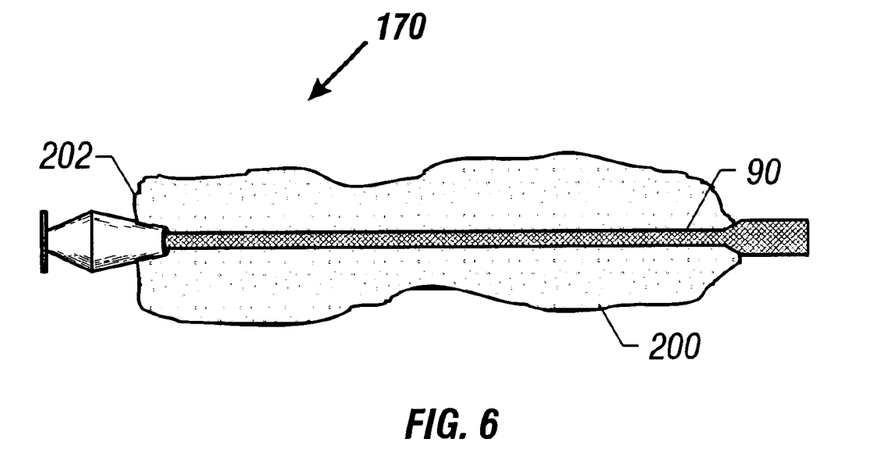
FIG. 6 is an elevation view of an alternative embodiment of a catheterization assembly in accordance with the present invention.
Figure 7:
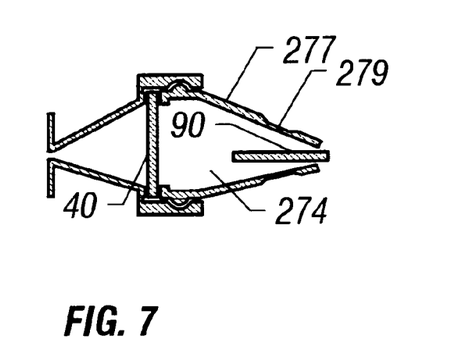
FIG. 7 is an enlarged cross sectional view of the catheter introducer portion of the catheterization assembly shown in FIG. 6.

Referring now to FIG. 6, another alternative embodiment of catheterization assembly 10 is shown. Catheter assembly 110 is similar to catheter assembly 10 but assembly 110 omits retaining collar 86 and includes a larger throughbore 274. Catheter guide member 170, shown enlarged in FIG. 7, is substantially conical or frustoconical in shape, and the proximal end 202 of sheath 200 is attached to the frustoconical region 277 at annular recess 279. The larger throughbore 274 provides adequate catheter support. In some cases, the embodiment of FIGS. 6 and 7 may be preferred over that of FIGS. 1–2 for ease of manufacture and for cost considerations.

While the preferred embodiments of the invention have been shown and described, modifications thereof can be made by one skilled in the art without departing from the spirit and teachings of the invention. The embodiments described herein are exemplary only, and are not limiting. Many variations and modifications of the invention and apparatus disclosed herein are possible and are within the scope of the invention. Accordingly, the scope of protection is not limited by the description set out above, but is only limited by the claims that follow, that scope including all equivalents of the subject matter of the claims.

What is claimed is:

1. A urinary catheterization assembly comprising:
   a catheter introducer member having a first end adapted for contacting a urethral opening and a second end adapted for receiving a catheter;
   a throughbore extending from a first opening at said first end to a second opening at said second end;
   a reservoir portion containing a lubricant chamber, said lubricant chamber disposed within said throughbore and terminating adjacent said first opening;
   a guide portion joined to said reservoir portion and terminating at said second end;
   a piercable membrane disposed in said throughbore at a position between said lubricant chamber and said guide portion and capable of retaining a lubricant in said lubricant chamber,
   wherein said first end of said catheter introducer member includes a body-contacting collar, and wherein said introducer member includes a frustoconical segment having its smallest outer diameter adjacent to said collar.

2. The catheterization assembly of claim 1 wherein said throughbore is of essentially uniform diameter from said first opening to said second opening.

3. The catheterization assembly of claim 1 wherein said lubricant chamber comprises an enlarged diameter portion of said throughbore.

4. The catheterization assembly of claim 1 wherein said reservoir portion and said guide portion are releasably joined together.

5. The catheterization assembly of claim 1 further comprising:
   a sheath having first and second ends, said first end being attached to said guide portion such that said throughbore second opening is enveloped by said sheath, said sheath second end being attached to a urinary catheter having proximal and distal ends such that when the proximal end of the catheter is situated in said throughbore, a length of the catheter between said proximal and distal ends is also enclosed by said sheath.

6. The catheterization assembly of claim 5 further comprising:
   a catheter having a first end extending through said throughbore second opening and into said throughbore, said first catheter end being capable of piercing said membrane when forced against said membrane.

7. The assembly of claim 6 wherein said throughbore has a portion with a tapered surface capable of guiding said catheter first end into said throughbore second opening.

8. The catheterization assembly of claim 6 wherein said sheath is of a length approximating said length of enveloped catheter such that when said sheath is fully extended lengthwise said sheath and said guide portion together maintain said catheter first end in an initial position within said throughbore that is between said second end and said pierceable membrane.

9. The catheterization assembly of claim 1 wherein said catheter introducer further comprises lubricant in said lubricant chamber, a removable closure on said first opening and a roughened outer surface portion.

10. The assembly of claim 1 wherein said lubricant chamber has a tapered surface and said membrane is disposed at the widest end of said tapered lubricant chamber.

11. The catheter assembly of claim 1 wherein said membrane is capable of being pierced by a catheter proximal end to form an aperture in said membrane.

12. The assembly of claim 1 wherein said membrane is disk-like.

13. The assembly of claim 12 wherein said membrane is scored.

14. The assembly of claim 12 wherein said membrane is slit.

15. The assembly of claim 12 wherein said membrane includes an annular ridge.

16. A urinary catheterization assembly comprising:
   a flexible catheter having a proximal end;
   a catheter guide portion having proximal and distal ends and a first throughbore;
   a reservoir portion having proximal and distal ends, said proximal end including a body-contacting collar adapted for contacting a urethral opening, an aperture in said proximal end, and a second throughbore defining an interior cavity, said reservoir portion being releasably joined to said catheter guide portion such that said first and second throughbores are aligned, and said reservoir portion including a frustoconical segment having its smallest outer diameter adjacent to said collar;
   a membrane disposed between said guide portion and said interior cavity;
   a lubricant initially disposed in said interior cavity; and
   a flexible sheath covering a predetermined length of said catheter and said guide portion distal end, said sheath having
      a proximal end circumferentially enclosing and fixedly joined to said guide portion distal end,
      a distal end circumferentially enclosing and fixedly joined to said catheter at a predetermined point spaced apart from said catheter proximal end, said sheath length being such that said sheath and said guide portion throughbore initially hold said catheter proximal end within said guide portion throughbore between said guide portion proximal and distal ends, said throughbores being able to slidingly receive said catheter.

17. The assembly of claim 16 wherein said guide portion and said reservoir portion are together a single monolithic structure and said membrane is fixedly disposed between said guide and reservoir portions.

18. The assembly of claim 16 wherein said guide portion and said reservoir portion are separate members that are detachably joined together.

19. The assembly of claim 18 wherein said guide portion further comprises an annular ridge and said reservoir further comprises an annular recess and said annular ridge and said annular recess are capable of being matingly and releasably joined.

20. The assembly of claim 18 wherein said membrane further comprises a raised resilient annular ring, said membrane and said annular ring being together a single monolithic structure, and said guide portion further comprises an annular lip capable of sealingly engaging said raised annular ring.

21. A kit for catheterizing a urinary bladder comprising:
a sterilizable catheterization assembly having a catheter introducer assembly with a catheter receiving end and a urethra contacting end;
  a throughbore in said introducer assembly extending from a first opening adjacent said urethra contacting end to a second opening adjacent said catheter receiving end,
  a reservoir portion disposed between said first and second openings and comprising a lubricant chamber that is axially aligned with said reservoir portion in said throughbore, said reservoir portion including a body-contacting collar adjacent said first opening and said reservoir portion including a frustoconical segment having its smallest outer diameter adjacent to said collar,
  a lubricant in said lubricant chamber, and
  a guide portion disposed between said reservoir and said second opening,
  a membrane in said throughbore disposed at a location between said lubricant chamber and said guide portion and capable of retaining said lubricant in said lubricant chamber, and
  a catheter having a proximal end, a body insertable portion and a distal end,
  a sheath member joined to said catheter guide and covering at least all of said catheter insertable portion, said sheath and said guide together holding said catheter proximal end in place within said catheter guide portion until said catheter is forced through said membrane when said catheter is used for its intended purpose;
  a sterility maintaining package enclosing said catheterization assembly; and
  at least one antiseptic swab.

22. A catheter introducer comprising:
a catheter receiving end and a body contacting end, said body contacting end including a body-contacting collar, and said introducer member including a frustoconical segment having its smallest outer diameter adjacent to said collar;
a throughbore extending from a first opening adjacent said body contacting end to a second opening adjacent said catheter receiving end;
a reservoir portion containing a lubricant chamber in said throughbore and terminating adjacent said first opening;
a guide portion joined to said reservoir portion and containing an elongated restricted diameter portion of said throughbore commencing adjacent said second opening and terminating adjacent said lubricant chamber, said restricted diameter portion adapted for supporting a sliding catheter tip; and
a membrane sealingly disposed in said throughbore between said lubricant chamber and said guide portion.

* * * * *